United States Patent [19]

Schaldach

[11] Patent Number: 5,447,523
[45] Date of Patent: Sep. 5, 1995

[54] PACEMAKER WITH PHYSIOLOGICAL CONTROL OF STIMULATION

[75] Inventor: Max Schaldach, Erlangen, Germany

[73] Assignee: Biotronik Mess-und Therapiegeräte GmbH & Co., Berlin, Germany

[21] Appl. No.: 277,290

[22] Filed: Jul. 22, 1994

Related U.S. Application Data

[63] Continuation of Ser. No. 803,895, Dec. 9, 1991, abandoned, which is a continuation of Ser. No. 459,536, Jan. 5, 1990, abandoned, which is a continuation of Ser. No. 832,004, Feb. 24, 1986, Pat. No. 4,919,137.

[30] Foreign Application Priority Data

Feb. 22, 1985 [DE] Germany .................. 35 06 791.8

[51] Int. Cl.6 .................................................. A61N 1/365
[52] U.S. Cl. ........................................................... 607/19
[58] Field of Search ................................. 607/19, 24–26

[56] References Cited

U.S. PATENT DOCUMENTS

| | | | |
|---|---|---|---|
| 4,126,139 | 11/1978 | Walters et al. | 128/419 PG |
| 4,428,378 | 1/1984 | Anderson et al. | 128/419 PG |
| 4,513,743 | 4/1985 | Van Arragon et al. | 128/419 PG |
| 4,527,568 | 7/1985 | Rickards | 607/625 |
| 4,541,430 | 9/1985 | Elmquist et al. | 128/419 PG |
| 4,552,154 | 12/1985 | Hartlaub | 128/417 PG |
| 4,600,017 | 7/1986 | Schroeppel | 128/419 P |
| 4,708,143 | 11/1987 | Schroeppel | 128/419 PG |
| 4,719,921 | 1/1988 | Chirife | 128/419 PG |
| 4,730,619 | 3/1988 | Koning et al. | 128/419 PG |

*Primary Examiner*—William E. Kamm
*Attorney, Agent, or Firm*—Spencer, Frank & Schneider

[57] ABSTRACT

A demand cardiac pacemaker implantable in a patient which includes a pulse generator which generates stimulating pulses at a controllable variable rate and has electrodes for applying stimulating pulses from the pulse generator to the heart of a patient. The length of the pre-ejection period (PEP) for the left ventricle in each heart cycle, which length is a function of the physiological demand of the patient, is detected and an output signal which is a function of the length of the pre-ejection period is produced. This output signal is used to control the pulse generator to produce stimulating pulses at a rate based on the output signal, and to apply the stimulating pulses to the electrodes in the absence of spontaneous heart action.

11 Claims, 3 Drawing Sheets

PACEMAKER WITH PHYSIOLOGICAL CONTROL OF STIMULATION

CROSS REFERENCE TO RELATED APPLICATION

This application is a Continuation of application Ser. No. 07/803,895, Filed Dec. 9, 1991, now abandoned, which is a continuation of application Ser. No. 07/459,536, Filed Jan. 5, 1990, now abandoned, which is a Continuation of Ser. No. 06/832,004, Filed Feb. 24, 1986, now U.S. Pat. No. 4,919,137 issued Apr. 24, 1990.

BACKGROUND OF THE INVENTION

The invention relates to a cardiac pacemaker.

Different attempts have been made to construct artificial cardiac pacemakers in which the stimulation frequency is adaptable to the patient's momentary physiological requirements.

Physiological control here means influencing the pacemaker so as to adapt the performance capability of the heart to the momentary requirements, i.e. particularly with respect to its basic rate which is independent of the prior patient specific regulation on the basis of electrical signals derived from the heart that were provided solely to avoid the simultaneous occurrence of stimulated pulses and spontaneous heart action.

Attempts in the past to use such a type of stimulation control over a broad range have failed because usually there is only an unclear relationship between the measured value employed and the stimulation rate which determines the heart output, or difficulties exist in finding suitable sensors which can be used for maintenance-free operation over longer periods of time—and particularly for implantation in the human body. Some of the physiological parameters previously used for demand dependent control are the saturation of the blood with oxygen, the blood temperature and the QT interval.

With the previously utilized measured values, it is not possible to set direct patient specific relationships between measured value and stimulated heart frequency since, in the human cardiovascular regulating system, complex functional, time specific dependencies must be considered between the parameters indicating physical stress and the resulting cardiac output. For accurate regulation corresponding to each individual case of stress for the patient, a patient specific adjustment would each time require that a stationary state be reached to permit a defined association of control parameter and heart rate. Since, however, the period of time within which a patient can be stressed is limited in time, inter alia because of the exhaustion of physical reserves—particularly if a cardiac illness exists—the necessary stationary state cannot be attained at all to the required extent. Due to the otherwise complex physiological relationships, regulation of the pacemaker frequency according to the known arrangements is therefore encumbered with considerable deviations in the frequency follow-up range so that physiological adaptation of the stimulation rate is not assured with the desirable reliability.

It is the object of the invention to derive a control algorithm from a physiological value which has a relationship to the heart frequency and thus permits more accurate follow-up of the heart frequency according to the patient's requirements.

SUMMARY OF THE INVENTION

The invention is here based, in particular, on the realization that the left-ventricular systolic time intervals have a functional relationship to the heart frequency, i.e. to the spacing between R waves, so that it is possible to process time relationships directly. Preferably, the parameters PEP (pre-ejection period), LVET (left-ventricular ejection time), the quotient of the above-mentioned values multiplied by some base time value and possibly these values in combination with the pulses derived from the heart and characterizing the electrical systole are applicable as systolic intervals (STI—Systolic Time Intervals).

The solution is here based particularly on the following relationships:

The systolic time intervals have an essentially linear relationship to the spacing between R waves. This relationship can be recorded for the respective patient by passing, once through the heart frequency range in question under ergonometric stress, with the stimulation rate being set each time by a external control unit to a value approximately corresponding to the stress or alternatively a value is selected from such a range which appears to be physiologically favorable and is associated with the corresponding physiological, time interval in a digital data memory. These values form reference points for an interpolation made during operation.

Correspondingly, in a preferred embodiment of the invention, if spontaneous actions of the ventricle are present, the association of respective systolic time intervals with various spontaneous frequencies of the heart may be recorded—possibly separately. The frequency values can also be used as reference points or control values, possibly using value which compensates for the deviations of the stimulated action from the spontaneous action under the physiological conditions existing in the heart. Information regarding a possible deviation of the systolic intervals with pacemaker intervention compared to spontaneous action can be obtained, in particular, during the transition from spontaneous to stimulated cardiac action with reference to the respectively last spontaneous frequency. For this purpose, the pacemaker is operated temporarily in each case in the demand mode, preferably upon completion of the stress cycle when the patient's heart frequency is decreasing, so as to follow the patient's decreasing heart frequency so closely that stimulation signals are supplied positively at regular intervals in a frequency pattern during the decreasing spontaneous heart activity so as to temporarily stimulate the patient's heart with a previously encountered higher (spontaneous) frequency. In this way, the functional relationship with the systolic intervals during stimulated operation can be recorded for the entire frequency range in question so that it is possible to determine for this operating state, if there is no spontaneous heart action, whether the momentary stimulation frequency corresponds to the momentary physiological conditions in every case.

By suitably storing the systolic interval data in memory locations assigned to the respective stimulation frequency it can thus be determined at a later date which stimulation frequency should be attempted to be attained in view of the momentary physiological conditions.

The use of systolic time intervals as physiological control values for the heart frequency also provides other advantageous possibilities: the systolic time intervals contain not only information regarding the momentarily physiologically favorable heart rate but are additionally dependent on the momentary chamber fill—and thus on the realizable volume per beat. The time interval developing for a momentary stimulation frequency is thus not a direct measure for the momentary frequency requirement, since upon stimulation with a frequency which deviates from this "physiologically correct" momentary frequency requirement, the chamber fill level at the actual frequency has an influence on the systolic time interval so that a conclusion as to the target frequency to be set can be made only indirectly.

With a step-wise approximation, the approach to the target frequency is made in small steps, with a continuous comparison of the direction of the deviation of the systolic time intervals with the direction of the change providing an additional check of the accuracy of the intended change. A further regulating possibility is given by a comparison of the resulting target frequency with the absolute values for the systolic time intervals stored for this target frequency.

These considerations apply for the case that no spontaneous actions occur which would permit a direct conclusion as to the rate desired by the heart itself. To make possible adaptation for spontaneous actions, it is favorable to keep the tendency of the stimulation produced in this manner in adaptation to the physiological conditions at a slightly lower level than the natural frequency belonging to corresponding conditions since otherwise possible spontaneous action would often be pre-empted by unnecessary stimulations.

If all possibilities of the method described here are utilized, advantages can be realized, particularly for the ischemic heart in which the relationship between volume per minute and heart frequency is nonlinear and is subject to fluctuations due to the existing damage, with certain heart frequencies which assure a good chamber fill to be preferred.

While for patients having an intact myocardium, the relationship between systolic time intervals and heart frequency is approximately linear, in the case of frequencies from a damaged myocardium, which permit only a reduced chamber fill, there results a shift toward smaller intervals, so that the resulting dependency has a "bulging" configuration. If a stimulation frequency is selected on the basis of the determined systolic time intervals, such frequency ranges should be preferred which, with reference to an imaginary line indicating an essentially linear curve, exhibit the greatest possible absolute LVET values. If the stimulated frequency changes due to changing intervals and under consideration of the above-described step-wise approximation, an interval change should first take place which leads to a new frequency value that also promises a favorable chamber fill. Such "favorable" stimulation rates, however, could also be preferentially selected in some other way. It is in order in this connection to perform the actually effected change in the stimulation frequency in small steps and to make the above-mentioned plausibility checks which confirm the selected change in direction and width. In practice, such a control is effected in that in the associated data memory those stimulation base rate values are replaced by data which are associated with the frequencies to be selected in these cases.

Since the systolic intervals are subject to additional fluctuations, the methods described here should preferably be employed statistically in that, for decisions which produce a change in the stimulation frequency, a sequence of systolic time intervals, or a pattern recorded at time intervals, is always selected in which the obtained values are averaged to increase reliability of the method. Advantageous features of statistical or digital regulating methods can be used here in addition, such as, for example, the change of the step length over time in the manner of a delta modulation.

The reliability of the method described here can be estimated without difficulty from the resulting convergence of the change steps. The patient's safety is assured in each case in that monitoring means for checking the direction of the changes and the number of changes or their plausibility, respectively, cause the system to be switched to operation at a fixed base rate.

The method described here can be used for pacemakers operating in various modes, with the single chamber pacemaker initially being preferred. If a change is made from ventricular to AV-sequential stimulation, it must be considered that in both cases separate functional dependencies must be considered, due to the different degree of chamber fill and the systolic intervals dependent on the stimulation mode, and these functional dependencies must be recorded in separate memories. Since otherwise conditions are analogous, it is possible to change from one mode to the other as desired—in each case with reference to corresponding stimulation frequencies—if conditions require.

Automatic adaptation of the stimulation frequency can be influenced by programming with respect to the frequency limits involved. For automatic adaptation corresponding to a "self-teaching process" which is also possible without running through a stress cycle under supervision of a physician on the basis of the changes in stress occurring during normal activity, the control range for stimulated frequencies would be adapted to that control range which would be covered if spontaneous actions were to occur.

The proper operation of the pacemaker, frequency controlled in the described manner, would be observable at any time without difficulty by the treating physician with utilization of the possibilities of two-way communications. Favorably, the external communications unit should here include an LCD display on which the functional dependency between the systolic time intervals and the stimulation frequency (distance between R waves) is graphically displayed in the values stored within the pacemaker. The degree of linearity resulting here for the recorded dependencies for one or a plurality of stress cycles in the manner stated above gives the physician a clear picture of the possibilities of the method described here with respect to the respective patient. By considering curvatures in the depicted functional relationships, preferred frequencies can be manually programmed externally into corresponding memory locations reserved for this purpose as they appear favorable to the physician for the respective case. In view of the individual programmability of the functional dependency of the stimulation frequency as the basic rate for the demand function or even for a pacemaker without this characteristic, the most varied aspects of a disease can be given consideration.

BRIEF DESCRIPTIONS OF THE DRAWING

The invention will be described in greater detail below together with a description of the preferred embodiment of the invention in reference to the drawing figures. It is wherein.

DESCRIPTION OF THE PREFERRED EMBODIMENTS

Figure 1:
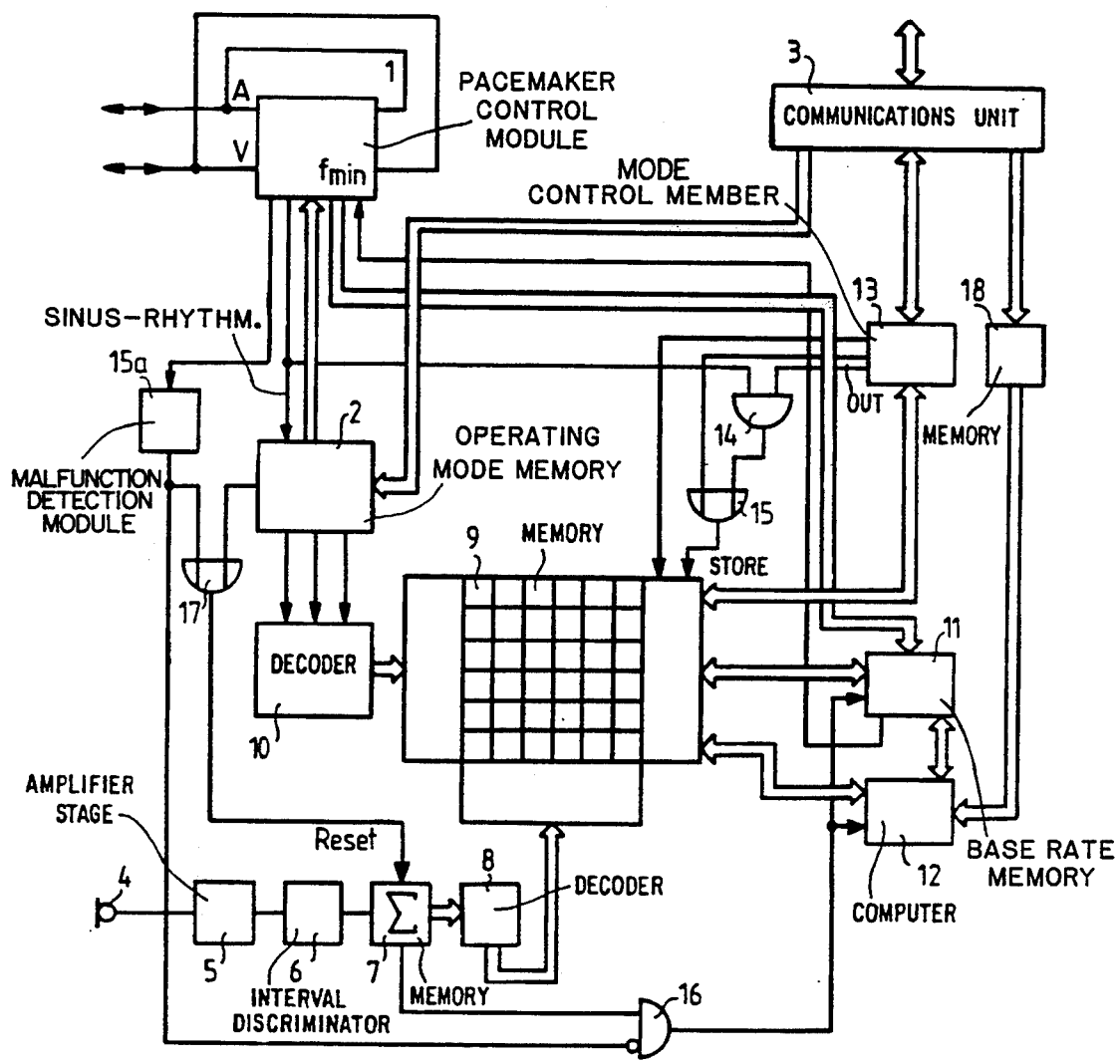
FIG. 1 is a block circuit diagram of an embodiment of the cardiac pacemaker according to the invention.

The block circuit diagram of the embodiment illustrated in FIG. 1 includes a conventional programmable atrium and/or ventricle pacemaker with demand function. The corresponding inputs and outputs to connect it with the atrium and ventricle electrode, respectively, are marked "A" and "V". The operating state of the control module 1 for the basic functions of the pacemaker is determined by a switching unit 2 for the operating states (modes) of the pacemaker and this switching unit can be influenced by means of a communication unit 3 and external programming means. Switching unit thus permits the setting of various operating states (VVI, DAT, DDD modes, etc.). In the illustrated pacemaker, the base rate or intervention frequency, which is set externally in prior art multiprogrammable pacemakers, can be programmed externally to go into the "physiological control" mode in which it adapts itself automatically to the patient's requirements by utilizing signals recorded from the patient's body.

As a particularity, the control module 1 illustrated here thus provides a terminal $f_{min}$ for influencing the basic frequency. The remaining modules shown in FIG. 1 are likewise combined in the implantable pacemaker housing.

The base rate, i.e. the escape interval, beginning with a preceding stimulated or spontaneous atrium or ventricle action and ending at the moment at which, in the absence of spontaneous action, stimulation occurs in the atrium or ventricle, can be changed by the remainder of the illustrated arrangement. The control is effected as a function of signals which are recorded acoustically within the patient's body, the left-ventricular systolic intervals. These signals are recorded by means of a microphone 4 which is designed as a vibration pickup and preferably includes a piezoceramic vibration transducer. The features of a vibration pickup suitable to implement the invention will be described in greater detail with reference to FIG. 3. The output signal of the vibration pickup is fed to an amplifier stage 5 which filters out the relevant frequency ranges and emits an output signal if signals of the selected frequencies are present for a given minimum period of time. The frequencies involved are preferably frequencies as they have been used in the past for phonocardiological examinations of the systolic intervals.

The output signal of stage 5 is fed to an interval discriminator 6 which—started by the leading edge of a first input pulse—determines the time that expires until the next pulse, with the first arriving pulse causing a reset and the evaluation being limited to a given time window after which, if it was without success, the measuring device will again be reset. If, however, two successive pulses appear within the time window, the time interval between their leading edges is put out as a digital signal and fed to a mean value memory 7 which forms a mean from a number of successive time interval values and stores this mean value.

The mean value is reset when the set pacemaker mode is changed (including by external programming) or if the stimulation state changes (transition from operation with action from the patient's heart back to stimulated operation, etc.) so that the mean value formation of successive systolic intervals is made only for similar operating states.

The output signal of mean value memory 7 is transmitted to an address decoder 8, with the addresses evaluated by the decoder being quantized by the selected digitalization according to the smallest step increases of the digital values so that the resolution of the time intervals to be evaluated always forms the difference between two adjacent memory addresses. Additionally, the address decoder converts the output signal of sum memory 7 in that it subtracts the minimum value of a systolic time interval to be evaluated from the digital input values and possibly adds additionally the address of the memory location (within a larger memory region). The memory 9 shown in FIG. 1 is organized in the form of a matrix, with the systolic time intervals addressing the columns while a further address decoder 10 which is influenced by operating mode memory 2 addresses the rows of the memory organized in the form of a matrix. In this way, it is accomplished that only the systolic time intervals for similar operating modes (spontaneous actions, ventricular or AV-sequential stimulation) are recorded. Upon a transition from one mode of operation to the other, mean value memory 7 is erased by way of its "reset" input and the mean value formation begins anew.

In an embodiment of the memory employing commercially available RAM elements, memory 9 will be configured in such a way that decoders 8 and 10 actuate different address lines, with both address signals forming a common binary address so that the address actuation coincides with that of customary microprocessor systems. The base rate included in the addressed memory values is transmitted by means of a base rate memory 11 into which they are taken over as buffer memory, with this value contained in the base rate memory determining the minimum stimulation frequency for the pacemaker circuit.

In this way a minimum stimulation rate is given as a function of the determined systolic time intervals and of the momentary mode of pacemaker operation and this stimulation rate corresponds physiologically to the determined systolic intervals. By initially setting up a table of the previously determined patient specific dependencies—as will be described below—the control is independent of further physiological dependencies which might influence the systolic time intervals if they have any connection with the base rate. If the determined intervals change, the base rate will gradually change as well, with the interval recorded to initiate the change not necessarily corresponding to that interval period which belongs to the target frequency to be set, unless the change in intervals to be considered until the target frequency is reached changes its sign. Thus, if deviations are noted, the illustrated control will slowly lead the stimulation frequency (also as a result of the operation of mean value memory 7) to the new physiologically required stimulation frequency, with the further interval changes to be traversed in the course of the approach not interfering with the realization of the final target frequency if the relationship between the recorded time interval and the associated pacemaker rate is unequivocal. The buffer memory for the base rate is activated each time by an "evaluation" signal which is derived from mean value memory 7 and signals the arrival of a new systolic interval value. In this operation, it is assumed that all frequency values in memory 9 have been transmitted externally from communications unit 3, with the communications unit setting the pacemaker, by means of a control member 13 subject to external programming, into the "read-out" state so that each address from a systolic time interval reads out the associated value stored in memory 9.

In an operating mode identified by control member 13 via the output "out" if action from the heart is present (corresponding output of pacemaker control module 1), the pacemaker operates with automatic storage in memory 9 of the spontaneous frequency belonging to certain systolic intervals so that these signals can also be utilized for stimulation that may become necessary later. The distance between two recorded identical spontaneous actions in the heart (within a physiologically justifiable range) is in this case transmitted by pacemaker member 1 to base rate memory 11 and is read into the respectively addressed memory location which in this case is associated, via operating mode addressing member 2, with action from the heart. In this case, the "store" input of memory 9 is linked, by means of an AND gate 14, via the "out" output of control member 13 the output signal "spontaneous action" of the pacemaker control module 1 and the "store" input of memory 9 is actuated via an OR gate 15.

Moreover, on the basis of the signals from the heart recorded by pacemaker member 1, the latter performs a tachycardia (and/or extrasystole) and malfunction detection which is processed by means of a corresponding module 15a. If such states occur, processing of the output signals from mean value memory 7 is blocked via the inverting input of an AND gate 16 inserted into the corresponding output of mean value memory 7. At the same time, an additional OR gate in the reset line of mean value memory 7 causes the latter to be reset to its starting state.

In the above-described storage of the actual systolic intervals during spontaneous action, the control is effected on the basis of the stored values during stimulation monitored by an additionally provided computer 12 which, actuated by a new interval signal recorded in the heart, is able to additionally change the associated base rate in memory 11 on the basis of additional information and values put in by communication unit 3, with access to memory 9 being possible. This change resides, in particular, in the provision of a correction value which, if the base rate of the pacemaker is regulated under stimulation conditions and the corresponding intervals during spontaneous action are evaluated, considers the change in the systolic intervals resulting due to the change in these conditions for the heart. Moreover, interpolation or compensation of the resulting frequency jumps can be compensated out in adjacent memory locations. Additionally, limit values 18 for the stimulation frequencies can be programmed in by way of communication unit 3 which values are not exceeded when the pacemaker base rate is adjusted. The corresponding limit value memory is read by the computer and if the respective value is exceeded due to regulation on the basis of the systolic intervals, a correction is made of the frequency value taken over into base rate memory 11.

Figure 1A:
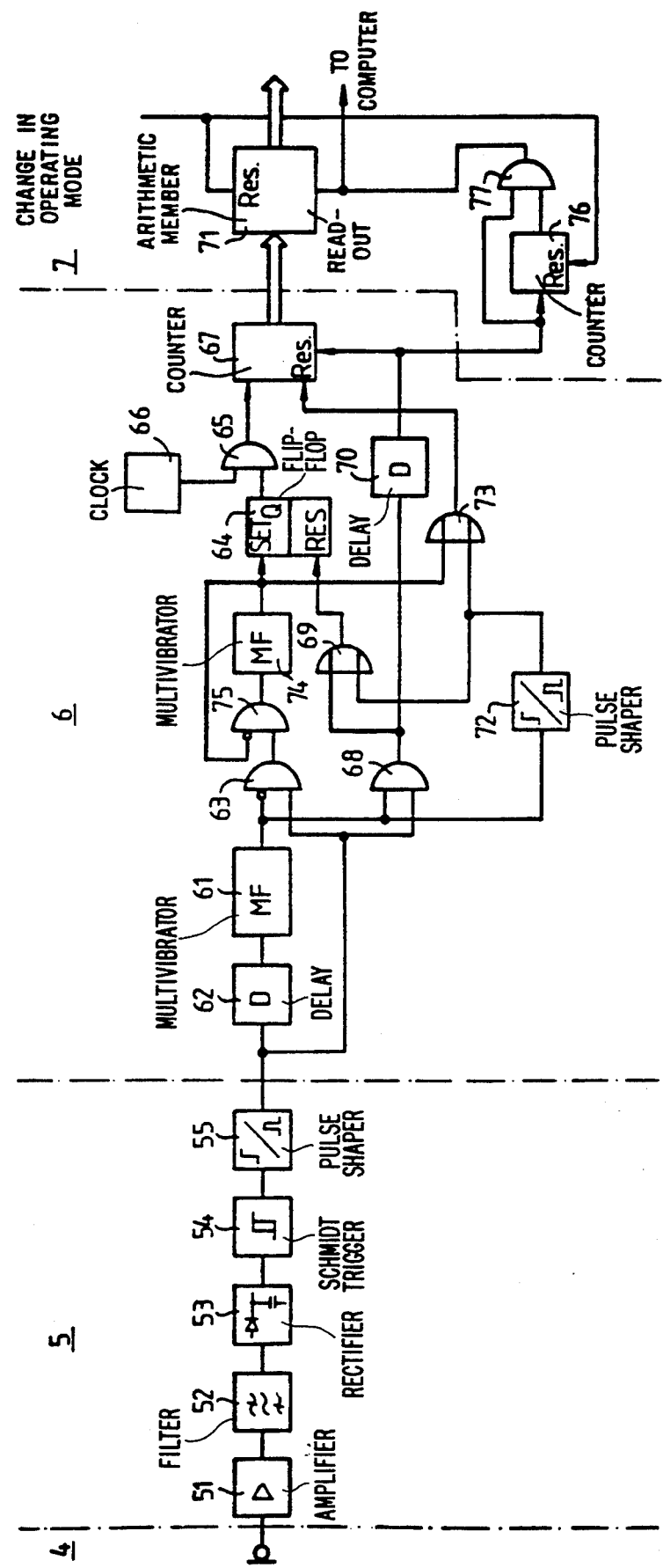
FIG. 1a is a detail view of the block circuit diagram of FIG. 1.

FIG. 1a is a detail view of the input portion of the circuit composed of modules 4 to 7. The processing group connected to microphone 4 is here composed of an input amplifier 51 to amplify the input signals, a filter 52 to filter out the frequency ranges characteristic of the systolic time intervals, a rectifier and filter member 53 for 54 conversion of the frequency signals into pulses of one polarity, a Schmitt trigger 54 as threshold value discriminator, and a pulse shaper 55 for converting the leading edge of the. Output pulse of circuit 54 into a short control pulse.

Time evaluating member 6 is composed of a monostable multivibrator 61 which receives the output signal of stage 5 with a delay by a few milliseconds imparted by a delay member 62. The pulse duration of the monostable multivibrator corresponds to the maximum systolic interval duration to be evaluated. If monoflop 61 is not set, the input signal passes through an AND gate 63 whose further (inverting) input is connected with the output of monoflop 61, to the "set" input of a flip-flop 64 which enables via its Q output an AND gate 65 so that a pulse signal generated by a clock pulse generator 66 reaches the corresponding input of a counter 67 so that the counter counts upward in correspondence with the expired time.

If monoflop 61 is set, the pulse terminating the systolic interval travels through an AND gate 68 and an OR gate 69 to the reset input of flip-flop 64 so that the counting process is interrupted. With a delay of a few milliseconds, the "read-out" input of counter 67 is activated by the output of AND gate 68 via a delay member 70 so that the determined counter state is transferred to the subsequent mean memory 7. At the end of the pulse duration of monoflop 61 and after conversion of the trailing edge into a control pulse in a pulse converter 72, flip-flop 64 and counter 67 are reset via OR gates 69 and 73, respectively without read-out taking place. By means of a further monoflop 74 which is inserted in the "set" line of flip-flop 64, the systolic time intervals are prevented from being evaluated in a sequence faster than what would correspond to the normal heart rate since an AND gate 75 in the input of the monoflop is blocked via its inverting input as long as its pulse has not decayed. The pulse duration of monoflop 74 here corresponds to the maximum spacing between R waves of the corresponding heart frequency to be processed.

Mean value memory 7 includes an arithmetic member 71 that forms the mean value of the previously recorded systolic intervals (here: LVET) under priority consideration of the last five events and stores this value. If there is a change in the operating state or a transition from stimulating operation to the rest state of the pacemaker with existing sinus rhythm, the arithmetic member 71 of the mean value memory is erased so that the mean value formation begins anew with the next systolic intervals recorded. Read-out from the mean value memory occurs with the input of every new mean value, after the latter has been processed. (Output: actuation of computer and activation of the output of the arithmetic member.) To reduce the frequency of changes in the stimulation frequency, the switching frequency can also be reduced by dividing it down. By means of a subsequently connected AND gate 77, a counter 76 blocks the output of determined interval values after a change in operating state, since in this case the counter is Set back ("reset" input) and emits an output signal to switch through AND gate 77 only if the counter state is > 5.

In the above-described storage of the actual systolic intervals during spontaneous action, the control is effected on the basis of the stored values during stimulation monitored by an additionally provided computer 12 which, actuated by a new interval signal recorded in the heart, is able to additionally change the associated base rate in memory 11 on the basis of additional information and values put in by communication unit 3, with access to memory 9 being possible. This change resides, in particular, in the provision of a correction value 10 which, if the base rate of the pacemaker is regulated under stimulation conditions and the corresponding intervals during spontaneous action are evaluated, considers the change in the systolic intervals resulting due to the change in these conditions for the heart. Moreover, interpolation or compensation of the resulting frequency jumps can be compensated out in adjacent memory locations. Additionally, limit values 18 for the stimulation frequencies can be programmed in by way of communication unit 3 which values are not exceeded when the pacemaker base rate is adjusted. The corresponding limit value memory is read by the computer and if the respective value is exceeded due to regulation on the basis of the systolic intervals, a correction is made of the frequency value taken over into base rate memory 11.

FIG. 1a is a detail view of the input portion of the circuit composed of modules 4 to 7. The processing group connected to microphone 4 is here composed of an input amplifier 51 to amplify the input signals, a filter 52 to filter out the frequency ranges characteristic of the systolic time intervals, a rectifier and filter member 53 for conversion of the frequency signals into pulses of one polarity, a Schmitt trigger 54 as threshold value discriminator and a pulse shaper 55 for converting the leading edge of the output pulse of circuit 54 into a short control pulse.

Figure 2:
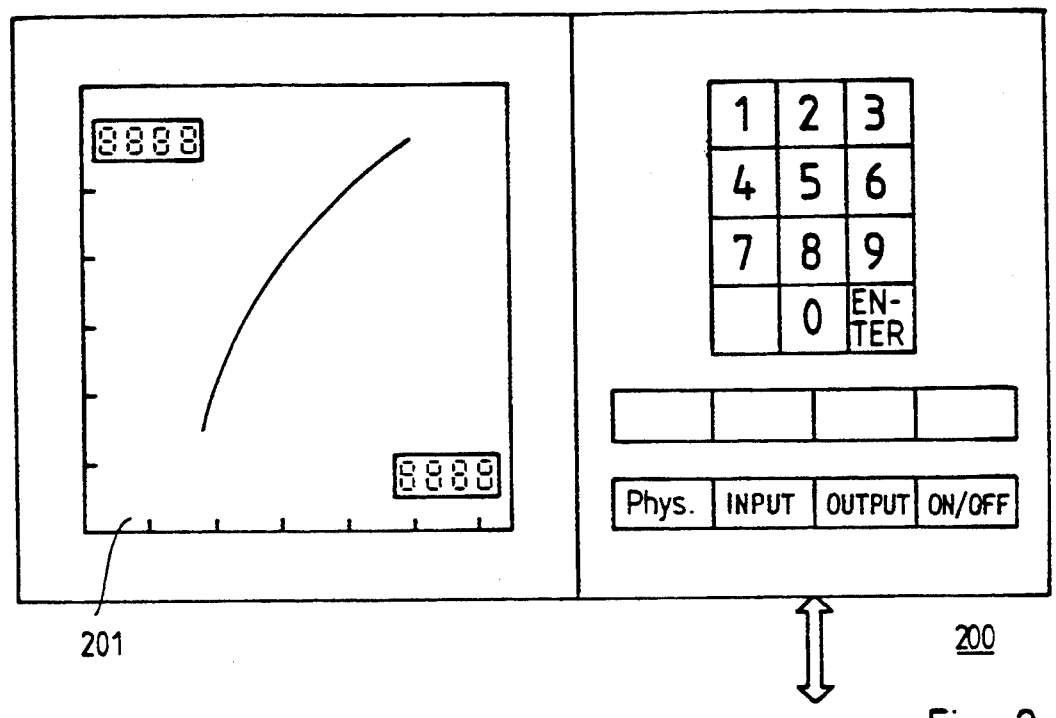
FIG. 2 is a communication member for external interrogation and control of the pacemaker by the physician.

FIG. 2 is a top view of a control member 200 for external programming and control by the physician's hands. On display 201 in the left half of the picture, the functional dependency of the heart frequency is shown in dependence on the systolic intervals to be detected, with the display being made separately (or superposed) for different operating states. The illustration corresponds to the values stored in pacemaker memory 9, with it being possible to either give a fixed functional relationship or the stimulation frequencies to be maintained for the systolic intervals determined in the implanted system are calculated on the basis of the values found when sinus rhythms did exist. It is also possible to program in preferred stimulation frequencies to be maintained for predetermined value ranges of the systolic intervals as well as differences in the frequencies which belong to interval values for different operating modes, so that these correction values can be used when the mode is changed, etc. Processing of the heart and stimulation frequencies takes place in the form of the (reciprocal) interval between R waves so that proportionality with the detected interval times is attained with respect to processing and inverse relationships are avoided.

Figure 3:
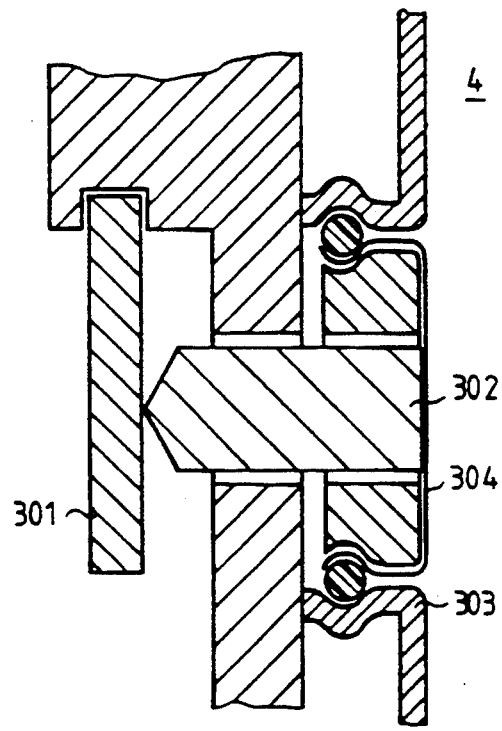
FIG. 3 is an enlarged sectional view of an acoustic sensor.

The vibration pickup shown in FIG. 3 can be accommodated in the pacemaker itself as well as in the electrode which is anchored in the heart. It includes a unilaterally clamped in piezotransducer 301 which is in communication, via a mechanical coupling element 302, with a membrane 304 which seals off the housing and wall 303, respectively.

The invention in its embodiments is not limited to the above described, preferred embodiment. Rather, a number of variations are conceivable which utilize the illustrated solution even in basically different embodiments. In particular, the invention is not limited to realization with discrete logic components but can also be realized to advantage with programmed logic systems—preferably with the use of a microprocessor.

I claim:

1. A demand cardiac pacemaker implantable in a patient, comprising: pulse generating means for generating stimulating pulses at a controllable variable rate; electrode means for applying stimulating pulses from said pulse generating means to the heart of a patient; means including a sensor for attachment to the heart, for detecting the length of the pre-ejection period (PEP) for the left ventricle in each heart cycle, which length is a function of the physiological demand of the patient, and for producing an output signal which is a function of the length of said pre-ejection period; and circuit means responsive to said output signal from said detecting means for controlling said pulse generating means to produce stimulating pulses at a rate based on said output signal from said detecting means, and for applying same to said electrode means in the absence of spontaneous heart action.

2. A cardiac pacemaker according to claim 1 wherein said sensor is a vibration pickup.

3. A cardiac pacemaker according to claim 1 wherein said sensor is a contact microphone.

4. A cardiac pacemaker according to claim 3 wherein: said microphone is a piezoelectric microphone having an output; and said means for detecting further includes a filter for passing a selected band of frequencies connected to said output of said piezoelectric microphone and a time selection means, connected to an output of said filter, for determining successive values of left ventricular systolic time intervals corresponding to the length of the pre-ejection period (PEP).

5. A demand cardiac pacemaker implantable in a patient, comprising:
   pulse generating means for generating stimulating pulses at a controllable variable rate;
   electrode means for applying stimulating pulses from said pulse generating means to the heart of a patient;
   means, including a sensor for attachment to the heart, for detecting the length of the pre-ejection period (PEP) in each heart cycle, which length is a function of the physiological demand of the patient, and for producing an output signal which is a function of the length of said pre-ejection period; and
   circuit means responsive to said output signal from said detecting means for controlling said pulse generating means to produce stimulating pulses at a rate based on said output signal from said detecting means, and for applying same to said electrode means in the absence of spontaneous heart action.

6. A cardiac pacemaker according to claim 5 wherein said sensor is a vibration pickup.

7. A cardiac pacemaker according to claim 5 wherein said sensor is a contact microphone.

8. A cardiac pacemaker according to claim 7 wherein:
   said microphone is a piezoelectric microphone having an output; and
   said means for detecting further includes a filter for passing a selected band of frequencies connected to said output of said piezoelectric microphone, and a time selection means, connected to an output of said filter, for determining successive values of systolic time intervals corresponding to the length of the pre-ejection period (PEP).

9. A demand cardiac pacemaker implantable in a patient, comprising:

pulse generating means for generating stimulating pulses at a controllable variable rate;

electrode means for a applying stimulating pulses from said pulse generating means to the heart of a patient;

means, including a sensor for attachment to the heart, for detecting a systolic time interval in each heart cycle, which interval is a function of the physiological demand of the patient, and for producing an output signal which is a function of the interval; and circuit means responsive to said output signal from said detecting means for controlling said pulse generating means to produce stimulating pulses at a rate based on said output signal from said detecting means, and for applying same to said electrode means in the absence of spontaneous heart action;

wherein said sensor is a vibration pickup.

10. A demand cardiac pacemaker implantable in a patient, comprising:

pulse generating means for generating stimulating pulses at a controllable variable rate;

electrode means for applying stimulating pulses from said pulse generating means to the heart of a patient;

means, including a sensor for attachment to the heart, for detecting a systolic time interval in each heart cycle, which interval is a function of the physiological demand of the patient, and for producing an output signal which is a function of the interval; and circuit means responsive to said output signal from said detecting means for controlling said pulse generating means to produce stimulating pulses at a rate based on said output signal from said detecting means, and for applying same to said electrode means in the absence of spontaneous heart action;

wherein said sensor is a contact microphone.

11. A cardiac pacemaker according to claim 10 wherein:

said microphone is a piezoelectric microphone having an output; and said means for detecting further includes a filter for passing a selected band of frequencies connected to said output of said piezoelectric microphone, and a time selection means, connected to an output of said filter, for determining successive values of systolic time intervals corresponding to the length of the pre-ejection period (PEP).

* * * * *